United States Patent
Hartrumpf et al.

(10) Patent No.: US 10,491,788 B2
(45) Date of Patent: Nov. 26, 2019

(54) APPARATUS AND METHOD FOR CONTROLLING THE QUALITY OF TRANSPARENT OBJECTS

(71) Applicants: Karlsruher Institut für Technologie, Karlsruhe (DE); Fraunhofer Gesellschaft Zur Förderung Der Angew. Forschung E.V., München (DE)

(72) Inventors: Matthias Hartrumpf, Karlsruhe (DE); Thomas Längle, Eggenstein (DE); Michael Heizmann, Eggenstein (DE); Henning Schulte, Karlsruhe (DE); Eduardo Monari, Karlsruhe (DE); Markus Vogelbacher, Baden-Baden (DE); Robin Gruna, Baden-Baden (DE)

(73) Assignees: Karlsruher Institut fur Technologie, Karlsruhe (DE); Fraunhofer Gesellschaft Zur Forderung Der Angew. Forschung E.V., Munich (DE)

( * ) Notice: Subject to any disclaimer, the term of this patent is extended or adjusted under 35 U.S.C. 154(b) by 226 days.

(21) Appl. No.: 14/845,725

(22) Filed: Sep. 4, 2015

(65) Prior Publication Data
US 2016/0072993 A1   Mar. 10, 2016

(30) Foreign Application Priority Data

Sep. 5, 2014   (DE) .................. 10 2014 217 771

(51) Int. Cl.
*G01N 21/90*   (2006.01)
*G01N 21/958*   (2006.01)
(Continued)

(52) U.S. Cl.
CPC ........... *H04N 5/2256* (2013.01); *G01N 21/90* (2013.01); *G01N 21/958* (2013.01);
(Continued)

(58) Field of Classification Search
None
See application file for complete search history.

(56) References Cited

U.S. PATENT DOCUMENTS 3,702,213 A  *  11/1972  Schwab ................ G02B 5/128
                                                                264/1.9
4,859,862 A      8/1989  Planke et al.
(Continued)

FOREIGN PATENT DOCUMENTS

EP        2269747 A1    1/2011
JP     2004279218 A    10/2004
(Continued)

OTHER PUBLICATIONS

Webb, Andrew R. et al., "Statistical Pattern Recognition," A John Wiley & Sons, Ltd., 3rd Edition.
(Continued)

*Primary Examiner* — Mikhail Itskovich
(74) *Attorney, Agent, or Firm* — Alix, Yale & Ristas, LLP

(57) ABSTRACT

The invention relates to an apparatus for controlling the quality of transparent objects, comprising at least one light source being adapted to illuminate the object, and at least one image capturing device, by means of which at least one image of the object can be detected, wherein the apparatus comprises further at least one reflector, wherein the reflector and the image capturing device define a beam path, wherein the reflector, the image capturing device, and the light source are arranged such that the object can be arranged between the reflector, on the one hand, and the image capturing
(Continued)

device and the light source, on the other hand, such that a single sheet of material is located in the beam path. Furthermore, the invention relates to a corresponding method for controlling the quality of transparent objects.

20 Claims, 5 Drawing Sheets

(51) Int. Cl.
  *G06T 7/40* (2017.01)
  *G06T 7/90* (2017.01)
  *H04N 5/225* (2006.01)
  *G06T 7/00* (2017.01)

(52) U.S. Cl.
  CPC .............. *G06T 7/0008* (2013.01); *G06T 7/40* (2013.01); *G06T 7/97* (2017.01); *G06T 2207/10148* (2013.01); *G06T 2207/10152* (2013.01); *G06T 2207/30108* (2013.01)

(56) References Cited

U.S. PATENT DOCUMENTS

| | | | | |
|---|---|---|---|---|
| 5,233,186 | A | * | 8/1993 | Ringlien ................ G01N 21/90 250/223 B |
| 5,495,330 | A | * | 2/1996 | Champaneri ...... G01N 21/9036 250/223 B |
| 8,422,003 | B2 | | 4/2013 | Hartrumpf et al. |
| 2008/0186693 | A1 | | 8/2008 | White et al. |
| 2013/0208105 | A1 | | 8/2013 | Schmidt et al. |

FOREIGN PATENT DOCUMENTS

| | | | | |
|---|---|---|---|---|
| JP | 2008268236 A | | 11/2008 | |
| JP | 2011149935 | * | 8/2011 | .............. G01N 21/90 |

OTHER PUBLICATIONS

European Search Report dated Jan. 15, 2016 (EP 15 18 3848).
H.B. Mitchell, Image Fusion: Theories, Techniques and Applications, 1st Edition Springer, 2010.

* cited by examiner

APPARATUS AND METHOD FOR CONTROLLING THE QUALITY OF TRANSPARENT OBJECTS

FIELD OF THE DISCLOSURE

The invention relates to an apparatus and a method for controlling the quality of transparent objects, comprising at least one light source which is adapted to illuminate the object and comprising at least one image capturing device, by means of which at least one image of the object can be captured. Apparatuses and methods of the above mentioned type can be used for inspecting container glasses in the pharmaceutical industry or food industry, for example.

BACKGROUND

It is known in practice to conduct a transmission inspection for controlling the quality of container glasses. This inspection is done by means of a camera which is directed through the opening of the container glass onto a diffuse illumination arranged below the bottom. The resulting camera image can be evaluated using electronic image processing or visual inspection by operators to thus detect contaminations, cracks or irregularities of form.

The drawback of such known systems is that the inspection work can only be accomplished inadequately when the bottoms have complex shapes. For example, the bottoms of container glasses are often provided with structural elements which can cause false-positive or false-negative inspection results when tested for contaminations.

Proceeding from this prior art, it is an object of the invention to provide an apparatus and a method for controlling the quality of transparent objects, the reliability of which is increased.

SUMMARY

In one embodiment, the invention relates to an apparatus for controlling the quality of transparent objects, comprising at least one light source being adapted to illuminate the object, and at least one image capturing device, by means of which at least one image of the object can be detected, wherein the apparatus comprises further at least one reflector, wherein the reflector and the image capturing device define a beam path, wherein the reflector, the image capturing device, and the light source are arranged such that the object can be arranged between the reflector, on the one hand, and the image capturing device and the light source, on the other hand, such that only a single sheet of material is located in the beam path.

In another embodiment, the invention relates to a method for controlling the quality of transparent objects, said method comprising the following steps: illuminating said object with at least one light source and capturing at least one image of the object using at least one image capturing device, wherein the object is located at least temporarily between a reflector, on the one hand, and the image capturing device and the light source, on the other hand, wherein at least two images of the transparent object are captured, wherein the relative orientation and position between the transparent object and the image capturing device are maintained and a first picture obtained using the reflector is compared with a second picture obtained using different shooting conditions.

The method proposed according to the invention also operates by means of a light source which is adapted to illuminate the object. The light source emits at least one spectral range in which the test object is transparent. In order to inspect containers made of transparent glass or plastic material, the light source can emit visible light. In order to control the quality of colored objects which are not transparent in the visible spectral range or are not transparent throughout the spectral range, the light source can also produce infrared or ultraviolet radiation which can penetrate the object to be inspected. Along with the spectral range used for the quality control, the light source can emit light of further spectral ranges. In some embodiments of the invention, the light source can be or contain a black body, e.g. an incandescent bulb or a halogen lamp. In other embodiments of the invention, the light source can be or contain an arc lamp. In yet another embodiment of the invention, the light source can be a gas discharge lamp or a semiconductor radiation source. A semiconductor radiation source can be selected from a light emitting diode, a superluminescence diode and/or a semiconductor laser.

The transparent object which shall be subjected to a quality control can be a container glass, for example. For the purposes of the present invention, a container glass can also consist of a plastic material, e.g. polyethylene. The container glass can be used in the food or pharmaceutical industry and be a beverage bottle, a jar, a syringe or an ampoule, for example. In other embodiments of the invention, the transparent object can be architectural glass, a vehicle glazing or another, generally known object, which can be penetrated by electromagnetic radiation in the selected spectral range.

Furthermore, the apparatus according to the invention has at least one image capturing device, by means of which at least one image of the object can be captured. The image capturing device can contain a photodiode or a photodiode array, for example. In other embodiments of the invention, the image capturing device can be or contain a line scan camera or a matrix CCD sensor. In addition, the image capturing device can contain a shutter element, an objective, an electronic control or further, generally known elements of electronic image capturing devices. The image capturing device used according to the invention is adapted to provide an analogous or digital data stream which represents an image of the transparent object to be inspected.

In some embodiments of the invention, several light sources can be available which illuminate the object from different angles, from different directions, with different polarization and/or with different spectral ranges. Correspondingly, in some embodiments of the invention, a plurality of image capturing devices can be available which capture the object with different magnification, from different directions or from a different distance. Different image capturing devices can also have an increased sensitivity for different polarization directions and/or different spectral ranges.

According to the invention, it is now proposed that the apparatus also contains at least one reflector, wherein the object can be placed between the reflector, on the one hand, and the image capturing device and the light source, on the other hand. This means that when the apparatus is operated, the light of the light source penetrates the object, is reflected on the reflector, again penetrates the object and is finally detected in the image capturing device.

The path of the reflected light depends on the kind of reflector used. In some embodiments of the invention, a model reflector can be used without beam displacement, i.e. every incident light beam is reflected back on exactly the same route. In some embodiments of the invention, it is possible to use a real reflector which in some embodiments of the invention has a minimum beam displacement resulting from manufacturing. For example, it is possible to use film reflectors which contain glass beads and/or microprisms. In the case of these reflectors, the detectable, reflected beam is weakened by absorption, on the one hand, and the reflected beam is widened since an incident model light ray results in a divergent bundle of rays.

In some embodiments of the invention, the reflector can be structured, i.e. the reflector consists of different regions which have different reflection properties. For example, the reflector can have first subareas which are covered with microprisms and second subareas which have no microprisms. In other embodiments of the invention, first subareas can have a first density and/or a first size of microprisms or glass beads and other regions can have a second density and/or a second size of microprisms or micro glass beads.

In some embodiments of the invention, it is possible to use a reflector which reflects incident light with a beam displacement which depends on the distance of the incident ray from the center of symmetry of the reflector. For example, it is possible to use prism reflectors or ball reflectors for carrying out the method according to the invention.

In some embodiments of the invention, various reflectors having different properties can be used, wherein a plurality of measurements or images of the object are made with different reflectors.

The apparatus according to the invention and/or the method according to the invention, which use a reflector, have the advantage compared to known images of the objects to be inspected in the bright field that the refraction on structural elements of the object is partly compensated for by the reflector. The compensation is the better, the smaller the return beam angle range and the smaller the distance of the reflector from the structural elements. In addition, defects and boundaries are imaged in a more high-contrast way since transmission changes have a square influence on the object image captured. In this way, a distinction between structural elements and contaminations is easily possible.

In some embodiments of the invention, the inspection of a bottom area of a container glass can be made by arranging the reflector in the exterior below the bottom of the container glass and disposing the image capturing device and the light source in the container or above the container opening since each point in the inner wall can be illuminated in this way. The refractive powers in the inner bottom region are usually considerably smaller than the refractive powers on structural elements of the bottom, and therefore each volume element of the bottom is screened. Since refractions on the structural elements are largely compensated for by the reflector, defects or contaminations can be imaged in a more high-contrast way. As only a single material layer of the container is arranged in the path of the beam, the evaluation of the data may be easier and/or more reliable.

In some embodiments, of the invention, a reflector may be introduced inside a hollow body under test, such as a container. Thereby, only a single material layer of the container is arranged in the path of the beam.

In some embodiments of the invention, at least two pictures of the transparent object are acquired, wherein the relative orientation and position between the transparent object and the image capturing device are maintained. In some embodiments of the invention, a first picture obtained using the reflector is compared with a second picture obtained using different shooting conditions. The differences in shooting conditions may be selected from any of the type or the distance of the reflector, the light source, the polarization or further parameters not explicitly mentioned. As the relative orientation and position between the transparent object and the image capturing device remains constant, corresponding features can be easily identified which may facilitate evaluation of the pictures.

In some embodiments of the invention, the distance between object and reflector can be changed. This allows to capture at least two images of the object, which differ at least by the distance of the reflector while the picture is taken. According to the invention, it has been found that the visibility of refractive structures is improved when the distance between object and reflector is increased. Thus, structural elements and characteristics of shape are shown in a more high-contrast way. However, the influence of absorbing structures, e.g. adhering contaminations, remains approximately equal. Thus, a distinction between refractive structures and inclusions and/or adhering contaminations can be made by comparing two object pictures which were taken at a different distance from the reflector.

In some embodiments of the invention, the apparatus further contains at least one dark field illumination. For the purposes of the present description, a dark field illumination is understood to mean an illumination where direct radiation of the light source does not reach the image capturing device. However, the light can be reflected or scattered by the object towards the image capturing device. Thus, the object appears to be bright in front of a dark background. In other embodiments of the invention, the material of the object can be lighted by stimulating the dark field illumination. In the case of such a fluorescence image, regions with deviating material, e.g. inclusions and flaws, can be detected by means of their difference in brightness. The light scatter on inclusions, e.g. particles or bubbles, can likewise be used for detecting the faulty material. These elements can be detected with high accuracy due to the light scatter on structural elements or contaminations.

In some embodiments of the invention, the reflector can have the shape of a cone. In other embodiments of the invention, the reflector can have the shape of a pyramid. Such a reflector can be arranged concentrically or coaxially in a rotationally symmetrical object to thus image the surrounding wall by means of the image capturing device. For example, the opening region of a beverage bottle can be inspected in this way, it being possible to also detect defects of a thread at the opening.

In some embodiments of the invention, the reflector can be arranged on at least one lateral cylinder surface. Here, the reflector can be arranged on the inner side of a hollow cylinder which surrounds the object to be inspected. In other embodiments of the invention, the reflector can be arranged on the exterior of a cylinder which can be introduced into a hollow body. As a result, the light source and/or the image capturing device can be arranged outside the hollow body, and therefore only minor limitations regarding the installation space have to be observed in connection with these components.

In some embodiments of the invention, the reflector can only cover a subarea on the lateral cylinder surface. For example, the reflector can cover an angular range of about 180° on the lateral cylinder surface. Thus, the remaining subarea of the lateral cylinder surface can be covered with either a reflector having different properties or a neutral background which can be used in connection with a dark field illumination, for example. Therefore, different images of the object can be captured by merely rotating the reflector-carrying cylinder by 180°.

In some embodiments of the invention, the light source can be arranged concentrically about the objective of the image capturing device. This characteristic has the effect that the emittance area of the light source covers approximately the acceptance area of the image capturing device. Therefore, the light cone of the light source is arranged approximately coaxially with the capturing area of the image capturing device. This allows a uniform illumination of the object and a high quality of the object images which are captured by the image capturing device and can be read out with minor flaws.

In some embodiments of the invention, the apparatus contains a beam splitter, via which the capturing area of the image capturing device and the light cone of the light source can be joined. This feature also has the effect that the light cone of the light source extends approximately coaxially with the capturing area of the image capturing device.

In some embodiments of the invention, the apparatus can also contain a device for producing a mechanical stress in the object. This device can be e.g. a collet chuck or a pin which acts on the object with a presettable force to thus produce a mechanical stress. In other embodiments of the invention, the device can produce an excess pressure or a negative pressure in an object for producing a mechanical stress so as to deform it. The capturing of at least one image by means of the image capturing device in the presence of a mechanical stress can be used to detect flaws in the object, e.g. by stress double refraction or by evaluation of the deformation and comparison with desired nominal values.

In some embodiments of the invention, the apparatus further contains at least one evaluation device by means of which the data of the image capturing device can be evaluated. The evaluation device is provided to compare at least two images of the object to be inspected and/or at least one image with a reference image or reference data to detect deviations regarding the quality of the object from a desired nominal quality. For this purpose, the evaluation device can contain electronic components, e.g. a microprocessor or a microcontroller. The evaluation device can also contain software which performs the desired evaluation of the data of the image capturing device when it runs on a microprocessor. In some embodiments of the invention, the evaluation device can be part of a control and/or feedback control device which fully automates the run of the inspection procedure according to the invention. In particular, a picturing device for the object to be inspected can be controlled via assigned actuators, the distance and/or the kind of a reflector can be controlled, the image capturing device can be controlled and/or at least one light source can be switched on or off.

In some embodiments of the invention, at least two images of the transparent object can be supplied to the evaluation device, wherein the evaluation device is adapted to compare at least one first image which was taken using the reflector with a second image the picturing conditions of which differ from the first image. In some embodiments of the invention, the second image can be produced using a different light source, which illuminates the object from different angles and/or from different directions and/or with different polarization and/or with different spectral ranges. Alternatively or additionally, it is possible to use an image capturing device for the second image, said image capturing device capturing the object with different magnification and/or from different directions and/or from a different distance and/or with an increased sensitivity to different polarization directions and/or different spectral ranges. Alternatively or additionally, the distance of the reflector can be extended for the second image and/or a reflector having different properties can be used.

In some embodiments of the invention, the transparent object can be transported between the first image and the second image from a first image taking station to a second image taking station. This allows an efficient use of the invention in production plants in which containers have to be transported between different stations anyway, e.g. a washing machine, a filling machine and a labeling machine. The transparent objects to be inspected can pass sequentially on a conveyor belt through the image capturing stations, and therefore different picturing conditions for the first image and the at least one second image can be produced rapidly and easily.

BRIEF DESCRIPTION OF THE DRAWINGS

The invention shall be explained in more detail below by means of figures without limitation of the general inventive concept, wherein.

DETAILED DESCRIPTION

Figure 1:
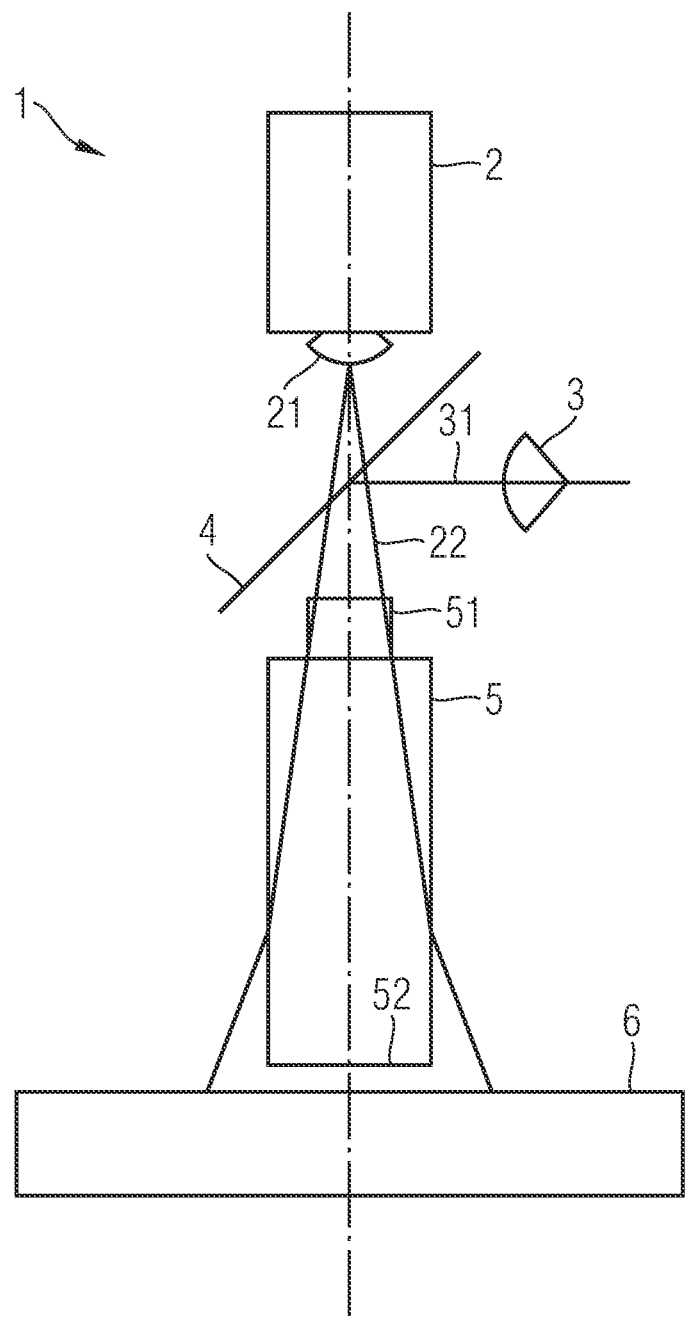
FIG. 1 shows a first measurement of an object 5 to be inspected according to the present invention with a first embodiment of the apparatus according to the invention.

FIG. 1 shows a first embodiment of the apparatus 1 according to the invention where a first method step is carried out. The apparatus 1 contains at least an image capturing device 2, a light source 3 and a reflector 6.

In some embodiments of the invention, the image capturing device 2 can be a generally known electronic camera which, e.g. by means of a CCD matrix detector, produces a data stream that represents an image of the object 5. The image taking device 2 can also have an objective 21 which images the object 5 on a sensor level.

For example, the reflector 6 can be or contain a generally known film reflector. The film reflector can contain glass beads and/or microprisms to reflect incident light without or with minimum beam displacement back into the direction of incidence. In the embodiment as shown, the reflector 6 is flat and even.

Furthermore, the apparatus contains a light source 3 which emits visible light and/or infrared radiation, for example. The light source 3 produces a light cone 31, which is reflected into the capturing area 22 of the image capturing device 2 via a beam splitter 4, and therefore the light cone 31 and the image capturing area 22 impinge approximately concentrically onto the object 5.

The object 5 is disposed between the reflector 6, on the one hand, and the light source 3 and the image capturing device 2, on the other hand. The object 5 can be received in a support (not shown), and therefore a plurality of objects 5 can be subjected to an inspection sequentially in automated fashion and/or the object 5 is movable and/or rotatable relative to apparatus 1. Due to this, different images of object 5 and/or different areas of object 5 can be subjected to an inspection.

In the exemplary embodiment as shown, the object 5 is a container glass, e.g. a beverage bottle or a glass for a preserve. Correspondingly, the object 5 has a bottom 52 and an opening 51. The bottom 52 can be provided with structural elements, e.g. a manufacturer designation or a bottom embossment which provides a slip-resistant surface of the container glass.

FIG. 1 shows the apparatus 1 during the conduction of a first method step for controlling the container bottom 52. During the first method step, the reflector 6 is in a first relative position to the container bottom 52. The distance between the reflector 2 and the container bottom 52 can be between about 0.5 mm and about 5 mm or between about 1 mm and about 3 mm, for example.

Figure 2:
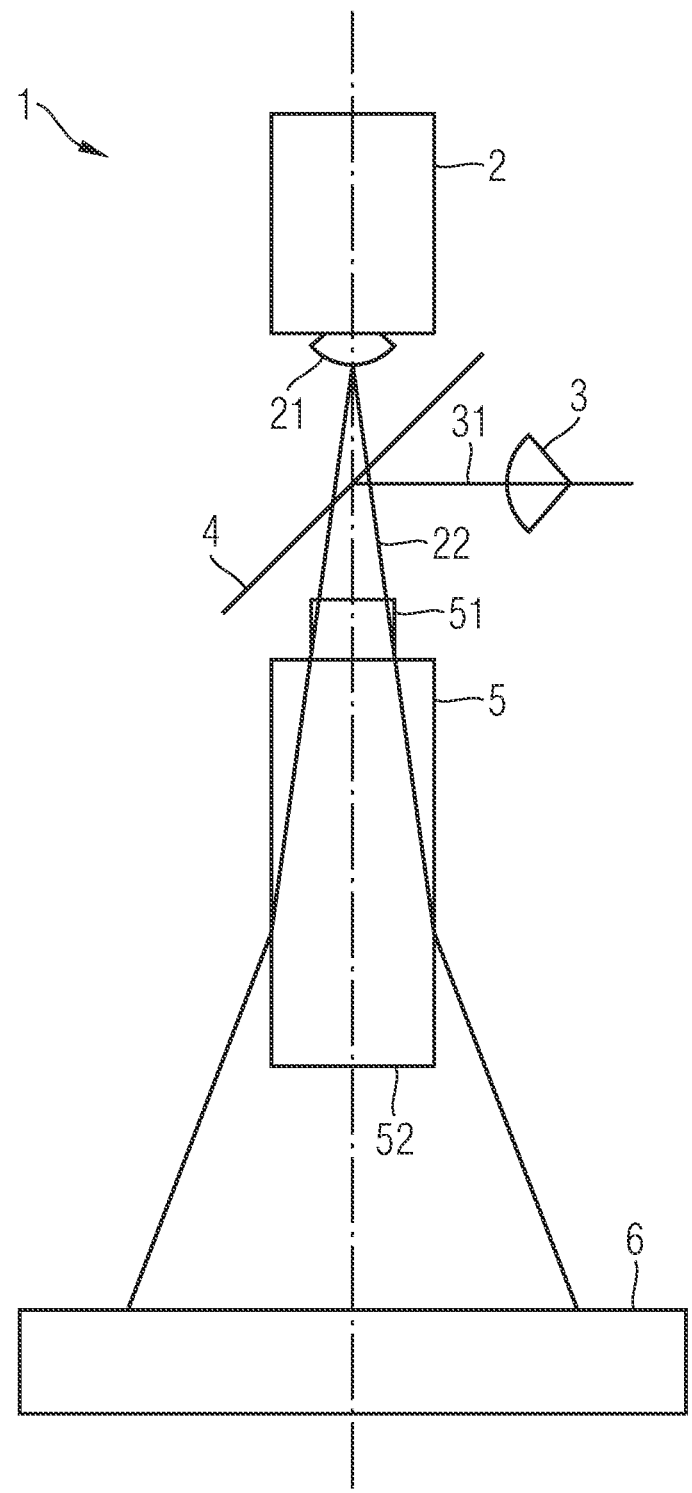
FIG. 2 shows a second measurement of the object 5 to be inspected with a first embodiment of the apparatus according to the invention.

FIG. 2 shows the apparatus 1 during the conduction of the second method step of the proposed inspection method. Equal reference signs designate equal elements of the invention, and therefore the below description is limited to the essential differences.

As evident in FIG. 2, the reflector 6 has a greater distance from the container bottom 52 when the second method step is carried out. The distance can be greater e.g. by a factor of 3 to a factor of 20 or by a factor of 5 to a factor of 15 compared to the conduction of the first method step. The extension of the distance between container bottom 52 and reflector 6 has the effect that the visibility of refractive structures increases. Such refractive structures can be structural elements and characteristics of shape of the container bottom 52, for example. However, the influence of absorbing structures, e.g. adhering dirt particles, remains approximately equal. Therefore, a distinction can be made between features of structure and contaminations by comparing the images of the image capturing device from the first method step and the images of the image capturing device from the second method step. When the measured results are compared with presettable nominal values which were either obtained with a model test object or determined theoretically, the quality of the structural elements can thus be determined and/or the presence of contaminations can be ruled out.

Figure 3:
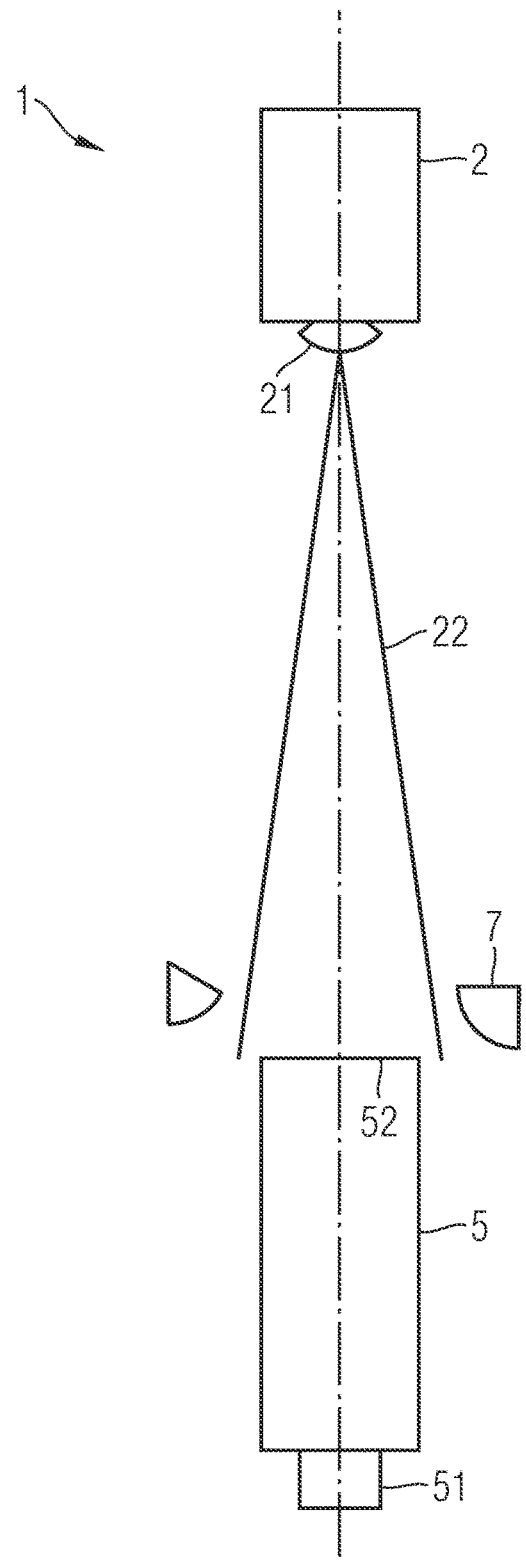
FIG. 3 shows a third measurement of the object to be inspected with a first embodiment of the apparatus according to the invention.

FIG. 3 shows the apparatus according to FIG. 1 in an optional third method step. In the third method step, the container bottom 52 of the object 5 is irradiated by a dark field illumination 7. The dark field illumination 7 provides a striping incident light beam, and therefore no light from the dark field illumination 7 can be incident in a direct way upon the objective 21 of the image capturing device 2. However, the light can be reflected or scattered on structural elements and/or contaminations, and therefore this scattered light is detectable with the image capturing device 2.

As is evident in FIG. 3, the dark field illumination 7 influences the exterior of the bottom 52 of the object 5 in the exemplary embodiment as shown. This means that the object 5 is either rotated with an assigned support (not shown) by 180° or the image capturing device 2 is moved about the object 5 or a second image capturing device is available which captures the light emitted from the dark field illumination 7 and reflected on the object 5.

The dark field illumination 7 effects an oriented excitation of the scattering of particles or structural elements on a side of the object. Thus, it can be established from a comparison of the data of the image capturing device from the third method step with the data of the image capturing device from the first and second method steps, for example, whether a contamination adheres to the inner or outer side of the object 5 and/or whether structural elements have the desired nominal form.

Figure 4:
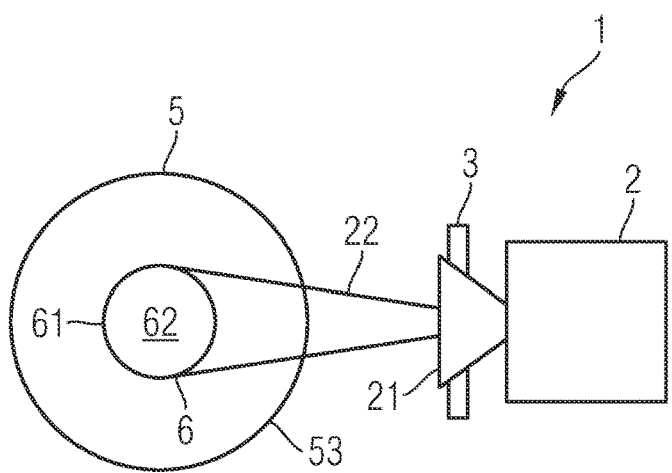
FIG. 4 shows a layout of a second embodiment of the apparatus.
Figure 5:
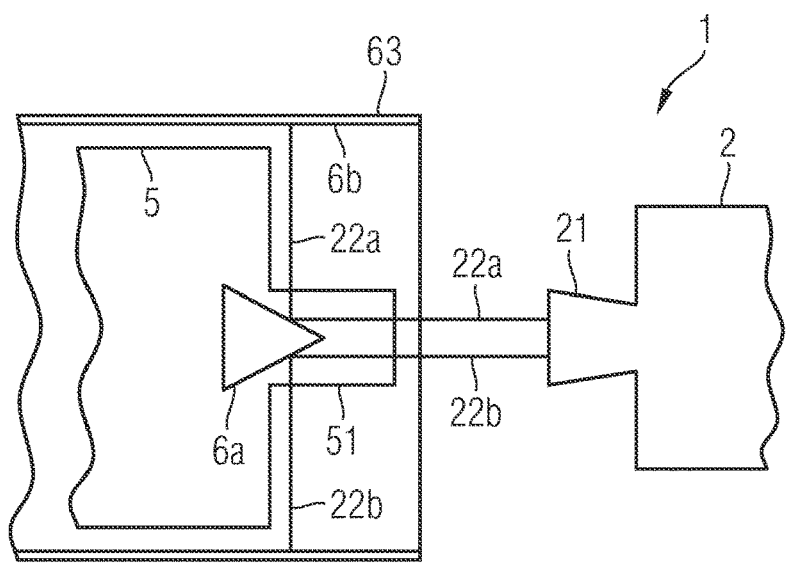
FIG. 5 shows a front elevation of a second embodiment of the apparatus.

Another embodiment of the apparatus 1 according to the invention is explained by means of FIGS. 4 and 5. Here, FIG. 4 shows a section or a layout and FIG. 5 shows the front elevation of the apparatus 1. Equal components are provided with equal reference signs, and therefore the below description is limited to the differences.

The apparatus 1 according to the second embodiment also uses an image capturing device 2 having an objective 21. Departing from the first embodiment, the light source 3 is arranged approximately annularly about the objective 21. In this case, too, the light cone of the light source 3 is approximately concentric relative to the capturing area 22 of the image capturing device 2.

The object 5 is also a container made of a transparent glass or plastic material, e.g. a beverage bottle having an opening 51 and a bottom 52 (not shown).

The apparatus 1 is provided to inspect the side wall 53. For this purpose, the reflector 6 is arranged at least on a subarea of the lateral surface of the cylinder 62. The cylinder 62 can be introduced through the opening 51 into the interior 54 of the object 5, and therefore light incident from the exterior via the side wall 53 is reflected on the reflector 6 and is reflected back to the image capturing device 2.

The cylinder 62 can be made so as to rotate and, on a further subarea, have a background 61 which can be used, for example, in connection with a dark field illumination and which largely absorbs incident radiation. Alternatively, the rear side of the cylinder 62 can be provided with another reflector, and therefore different images of the side wall 53 can be taken by rotating the cylinder 62.

In some embodiments of the invention, the object 5 is also rotatable relative to the image capturing device 2 and the light source 3, and therefore the entire lateral surface can be inspected by the apparatus 1.

Figure 6:
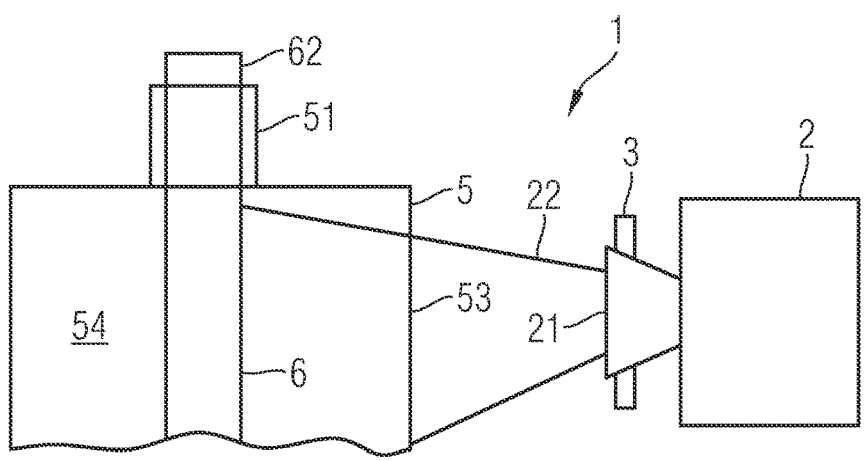
FIG. 6 shows a front elevation of a third embodiment of the apparatus.

FIG. 6 shows a third embodiment of the apparatus 1. The third embodiment also contains an image capturing device 2 having an objective 21. Furthermore, the third embodiment is also provided with a light source which is, however, not shown in FIG. 6. For example, the light source 3 shown in FIG. 4 or FIG. 1 can also be combined with the third embodiment according to FIG. 6.

FIG. 6 additionally shows an object 5 which, in this case, too, is a container glass having an opening 51. The opening 51 can have a thread which enables the unscrewing of a closure element.

In order to examine the opening area 51, a first reflector 6a is provided which has the shape of a pyramid or a cone, for example. The first reflector 6a can be introduced into the object 5 through the opening 51 and can be positioned in the opening area.

Furthermore, the apparatus has a second reflector 6b which is arranged on the inner side of a lateral cylinder area of a hollow cylinder 63. The hollow cylinder 63 is provided to receive the object 5 in the interior thereof.

Two optical paths 22a and 22b are shown by way of example and impinge on different subareas of the first reflector 6a where they are reflected at an angle of approximately 90°. In this case, the light rays penetrate the opening area 51 and are reflected on the second reflector 6b back into the direction of incidence, and therefore each light ray passes through the object 5 twice.

By capturing a plurality of images by means of the image capturing device 2 which are distinguished e.g. as regards the type of employed reflectors, the wavelength of light, the polarization direction or further parameters, several images of the opening 51 can be taken and supplied to an evaluation device. It is thus possible to determine the form and/or the contamination of the opening 51. In particular, the form of an external thread at the opening 51 can be inspected, and therefore only container glasses with complete thread are used in a subsequent process.

Figure 7:
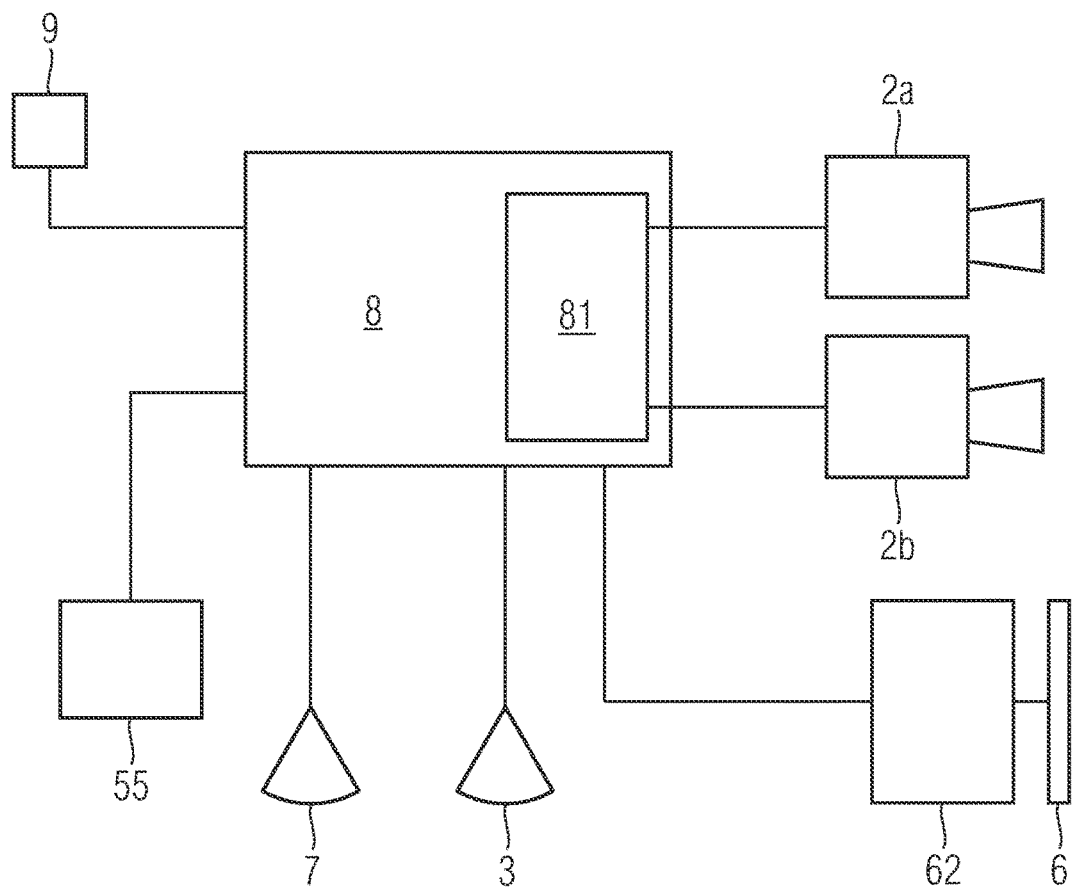
FIG. 7 shows a block diagram of the apparatus according to the invention.

FIG. 7 shows a block diagram of an apparatus 1 according to the invention. The apparatus 1 contains at least one image capturing device 2a. In the exemplary embodiment shown, two image capturing devices 2a and 2b are illustrated by means of which images of the test object can be taken in different spectral ranges, with different polarization, at a different distance and/or from different directions.

Furthermore, the apparatus 1 has an optional actuator 62 by means of which the reflector 6 can be moved. The actuator 62 can be a rotatable cylinder or a linear drive, for example, by means of which it is possible to change the distance of a flat reflector 6 from the test object.

As already explained above, the apparatus 1 has at least one light source 3, the light of which is emitted approximately concentrically to the capturing area of the image capturing devices 2. Several light sources 3 can be optionally present and emit light of different wavelength and/or different polarization.

In some embodiments of the invention, an optional dark field illumination 7 can be available to enable dark field images of the object.

The object as such can be mounted on an optional manipulator or a support 55 which enables a relative movement between the reflector, the image capturing device and the light source, on the one hand, and the test object, on the other hand. For this purpose, the manipulator 55 can contain a goniometer, a hexapod, a rotary table or other, generally known components.

In some embodiments of the invention, the apparatus 1 has an optional device 9 for producing a mechanical stress in the object 5. The device 9 can apply an excess pressure or negative pressure to the object 5 or exert a mechanical force by clamping, for example. For this purpose, the device 9 can contain a hydraulic or mechanical actuator, a vacuum pump, a compressor or other, similar devices.

The individual components of the apparatus 1 can be controlled by means of a control and/or feedback-control device 8, and therefore, a presettable test program having a plurality of test steps is conducted in automated fashion to carry out the inspection of an object. For this purpose, the control and/or feedback-control device 8 can contain a microprocessor or a microcontroller, on which a corresponding program runs that switches on or off the light sources 3 and 7, triggers the image capturing devices 2a and 2b or switches actuators, such as the actuator 62, the retaining apparatus 55 or the device 9.

Furthermore, an evaluation device 81 can be available which evaluates the data received from the image capturing devices 2a and 2b and/or compares them with reference data.

Of course, the invention is not limited to the embodiments shown in the drawings. Therefore, the above description should not be considered limiting but explanatory. The below claims should be comprehended in such a way that a feature mentioned is present in at least one embodiment of the invention. This does not rule out the presence of further features. In so far as the claims and the above description define "first" and "second" features, this designation serves for distinguishing two similar features without determining an order.

The invention claimed is:

1. An apparatus for conducting an inspection of transparent objects comprising:
    at least one light source directing illumination toward a transparent object to be inspected;
    at least one reflector movable by an actuator between a first position outside the transparent object at a first distance from an exterior of the transparent object being inspected and a second position outside the transparent object at a second distance from the exterior of the transparent object being inspected, said second distance being greater than said first distance;
    at least one image capturing device arranged to capture an image of the transparent object being inspected, said image comprising illumination that has passed through the transparent object and reflected off said at least one reflector; and
    an evaluation device including at least one microprocessor or microcontroller and a software,
    wherein said apparatus is configured to capture first and second images of a transparent object placed between the at least one reflector and the at least one image capturing device, said at least one image capturing device capturing the first image when said reflector is in said first position and the second image when said reflector is in said second position, said second position increasing visibility of refractive structures corresponding to structural elements of the transparent object while visibility of absorbing or scattering structures corresponding to inclusions or adhering contaminations of the transparent object remain approximately equal to said first position, the evaluation device operatively connected to receive the first image and the second image, said software comparing the first image to the second image when executed on said microprocessor or microcontroller, said comparison producing a result based upon distinguishing said refractive structures having increased visibility in said second image from said absorbing or scattering structures, and said result is compared with presettable nominal values to detect the quality of the transparent object.

2. The apparatus according to claim 1, wherein said apparatus is configured to alter an imaging condition under which the second image is captured, said imaging condition includes a type of light source, a spectral range of light generated by the light source, a polarization of the light source, a direction of illumination, a mechanical stress on said transparent object, a position of the image capturing device relative to the transparent object, a magnification of the transparent object by the image capturing device, a sensitivity of the image capturing device to polarization or different spectral ranges, and properties of the reflector.

3. The apparatus according to claim 1, comprising a first image acquisition station and a second image acquisition station,
    wherein said apparatus captures said first image at said first image acquisition station and captures said second image at said second image acquisition station.

4. The apparatus according to claim 1, wherein a dark field illumination is used.

5. The apparatus according to claim 1, wherein the reflector is arranged on at least one lateral cylindrical surface.

6. The apparatus according to claim 1, wherein the image capturing device includes a lens and the light source is arranged concentrically about the lens.

7. The apparatus according to claim 1, wherein the apparatus comprises a beam splitter, said image capturing device includes a capturing area, said light source produces a light cone, and said beam splitter joins the capturing area and the light cone.

8. A method for conducting an inspection of transparent objects comprising:
positioning a transparent object between at least one reflector and at least one image capturing device;
illuminating the transparent object with at least one light source such that light from said at least one light source is reflected by the at least one reflector toward said at least one image capturing device after passing through said transparent object;
capturing a first image of said transparent object with said at least one reflector in a first position outside the transparent object at a first distance from an exterior of the transparent object;
moving said at least one reflector to a second position outside the transparent object at a second distance from the exterior of the transparent object, said second distance being greater than said first distance and increasing visibility of refractive structures corresponding to structural elements of the transparent object while visibility of absorbing structures corresponding to defects of the transparent object remains approximately equal to said first position;
capturing a second image of said transparent object with said at least one reflector in said second position;
comparing said first image with said second image in an evaluation device to produce a result based upon distinguishing refractive structures having increased visibility in said second image from absorbing structures; and
comparing said result with presettable nominal values to detect the quality of the transparent object.

9. The method according to claim 8, comprising the step of altering the imaging condition after capturing said first image, the imaging condition comprising a type of light source, a spectral range of light generated by the light source, a polarization of the light source, a direction of illumination, a mechanical stress on said transparent object, a position of the image capturing device relative to the transparent object, a magnification of the transparent object by the image capturing device, a sensitivity of the image capturing device to polarization or different spectral ranges, and properties of the reflector.

10. The method according to claim 8, wherein the steps of capturing a first image and capturing a second image includes providing a first image acquisition station and a second image acquisition station,
wherein the step of capturing a first image occurs at said first image acquisition station and the step of capturing a second image occurs at said second image acquisition station.

11. The method according to claim 8, comprising the step of maintaining the orientation of the transparent object relative to the image capturing device during said steps of capturing said first image and capturing said second image.

12. The method according to claim 8, wherein the step of illuminating the transparent object includes using a dark field illumination.

13. The apparatus according to claim 1, wherein the reflector has different regions having different properties.

14. The apparatus according to claim 13, wherein at least one of said different regions comprises microprisms or glass beads.

15. The apparatus according to claim 13, wherein at least one of said different regions comprises microprisms or glass beads of different size or density.

16. The apparatus of claim 1, wherein when said software is executed on said microprocessor or microcontroller, said software determines a quality of said transparent object by comparing said first image and said second image with a reference image or reference data.

17. An apparatus for conducting an inspection of transparent objects comprising:
at least one light source directing illumination toward a transparent object to be inspected;
at least one reflector movable by a manipulator between a first position outside the transparent object at a first distance from an exterior of the transparent object being inspected and a second position outside the transparent object at a second distance from the exterior of the transparent object being inspected, said second distance being greater than said first distance;
at least one image capturing device arranged to capture an image of the transparent object being inspected, said image comprising illumination that has passed through the transparent object and reflected off said at least one reflector;
the manipulator enabling relative movement between the at least one light source, the at least one reflector, and the at least one image capturing device; a control unit controlling function of at least one of the at least one light source, the at least one reflector, the at least one image capturing device, or the manipulator; and
an evaluation device including at least one microprocessor or microcontroller and a software,
wherein said apparatus is configured to capture first and second images of a transparent object placed between the at least one reflector and the at least one image capturing device, said at least one image capturing device capturing the first image when said reflector is in said first position and the second image when said reflector is in said second position, said second position increasing visibility of refractive structures corresponding to structural elements of the transparent object while visibility of absorbing or scattering structures corresponding to inclusions or adhering contaminations of the transparent object remain approximately equal to said first position, the evaluation device operatively connected to receive the first image and the second image, said software comparing the first image to the second image when executed on said microprocessor or microcontroller, said comparison producing a result based upon distinguishing said refractive structures having increased visibility in said second image from said absorbing or scattering structures, and said result is compared with presettable nominal values to detect the quality of the transparent object.

18. The apparatus according to claim 17, wherein the control unit has a a microprocessor or a microcontroller which runs a presettable test program comprising a plurality of automated test steps conducted to inspect the transparent object.

19. The apparatus according to claim 17, wherein the control unit is a feedback-control unit.

20. The apparatus according to claim 17, wherein the control unit is a feedback-control unit having a microprocessor or a microcontroller which runs a presettable test program comprising a plurality of automated test steps conducted to inspect the transparent object.

* * * * *